(12) United States Patent
Castillo (10) Patent No.: US 10,717,717 B1
(45) Date of Patent: *Jul. 21, 2020

(54) ACTIVE FRACTION FROM THERAPEUTIC CANNABIS PLANT EXTRACTS

(71) Applicant: Jenny's Rose, LLC, Los Angeles, CA (US)

(72) Inventor: James Castillo, San Diego, CA (US)

(73) Assignee: Jenny's Rose, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/569,535

(22) Filed: Sep. 12, 2019

Related U.S. Application Data (63) Continuation-in-part of application No. 16/365,614, filed on Mar. 26, 2019, now Pat. No. 10,471,113.

(51) Int. Cl.
*A61K 36/00* (2006.01)
*C07D 311/80* (2006.01)

(52) U.S. Cl.
CPC .................. *C07D 311/80* (2013.01)

(58) Field of Classification Search
CPC ....................................... A61K 36/00
USPC ........................................................ 424/725
See application file for complete search history.

(56) References Cited

U.S. PATENT DOCUMENTS 9,351,953 B2 5/2016 Stodola
10,195,159 B2 2/2019 Whittle et al.

FOREIGN PATENT DOCUMENTS

WO 2018187500 A1 11/2018

*Primary Examiner* — Michael V Meller
(74) *Attorney, Agent, or Firm* — Stefan J. Kirchanski; Matthew J. Spark; Zuber Lawler & Del Duca LLP (57) ABSTRACT

An improved process for producing various types of *cannabis* extract from harvested *cannabis* wherein a quantity of harvested *cannabis*, which typically includes the inflorescence, floral leaves, and small stems of a flowering *cannabis* plants, is frozen and subjected to cryogenic grinding to produce pulverized *cannabis*. The pulverized *cannabis* is then subjected to alcohol extraction to produce an initial *cannabis* extract which is filtered to yield a remainder fraction and a filtrate. The remainder fraction potentiates the activity of *cannabis* formulations while the filtrate can be subjected to one of several forms of further processing according to the desired chemical profile of the final product.

2 Claims, 5 Drawing Sheets

ACTIVE FRACTION FROM THERAPEUTIC CANNABIS PLANT EXTRACTS

CROSS-REFERENCE TO PRIOR APPLICATIONS

The present application is a continuation-in-part of U.S. patent application Ser. No. 16/365,614, now U.S. Pat. No. 10,471,113, titled PRODUCING *CANNABIS* EXTRACTS VIA SELECTIVE DECARBOXYLATION, filed on 26 Mar. 2019, the contents of which are incorporated herein by reference.

U.S. GOVERNMENT SUPPORT

Not applicable.

BACKGROUND OF THE INVENTION

Area of the Art

The present invention is in the art of extracting natural products from plant materials and is more specifically directed to a process for making *cannabis* extracts.

Background of the Invention

The *cannabis* plant (*Cannabis sativa* L.) ("*cannabis*") has a long history use for both medicinal and recreational purposes. *Cannabis* plant material contains a variety of chemical compounds, including those responsible for the "high" associated with *cannabis* consumption as well as other physiological effects. Among the compounds present in *cannabis* are tetrahydrocannabinolic acid ("THCA") and tetrahydrocannabivaric acid ("THCVA"). While THCA and THCVA themselves produce few physiological effects when directly ingested, exposing THCA and THCVA to elevated temperatures, such as those produced when *cannabis* burns during smoking, causes these compounds to undergo a decarboxylation reactions to form psychoactive or other physiologically active compounds. THCA, in particular, is well-known for its conversion via decarboxylation to Δ9-tetrahydrocannabinol ("Δ9-THC"), which is psychoactive. Upon heating, THCVA undergoes a similar decarboxylation reaction to form tetrahydrocannabivarin ("THCV"), which has appetite-suppressing effects.

As of August 2019, ten U.S. states have legalized the recreational use of *cannabis*, and thirty-two U.S. states have legalized the use of all *cannabis* products for medicinal purposes while an additional five states allow use of CBD oil. As the state-level legalization of *cannabis* has expanded, so has the production of *cannabis*-derived products. *Cannabis* extracts (sometimes known as "*cannabis* oils") have emerged as an important category of *cannabis*-derived product. *Cannabis* extracts are produced by subjecting *cannabis* to an extraction process, wherein solvents are typically used to dissolve ("extract") chemical compounds from harvested *cannabis* plant material.

However, in the typical extraction process, the goal is to obtain purified extracts containing high concentrations of the cannabinoids, and discarding portions of the extract containing waxes, lipids, and other components of plant materials that do not contain the desired cannabinoids. As such portions of the extracts do not contain cannabinoids, they are not believed to possess therapeutic or commercial value.

For example, U.S. Pat. No. 10,195,159 (the '159 patent) describes a process for removing what it describes as the unwanted "ballast" from *cannabis* plant extracts. The ballast described therein includes plant cell constituents comprising "fats, waxes, carbohydrates, proteins and sugars." The '159 patent inventors explain that "[t]he presence of these substances results in botanical extracts which may be hygroscopic, difficult to reduce to a powder and generally intractable as starting materials for pharmaceutical preparations." In addition, the '159 patent explains "that presence of ballast may also limit the shelf-life of pharmaceutical products formulated from such extracts." The '159 patent also explains that some elements of ballast can be "removed by an additional step post-extraction referred to as "winterization", which involves making a concentrated solution of the extract and cooling it to a temperature at which a proportion of waxes and lipid components may be precipitated, typically −20° C."

WO2018187500A1 (the '500 application) describes a process for removing waxes and lipids from crude *cannabis* extracts before the process of decarboxylation and purification of the extracts to obtain purified *cannabis* extracts. The '500 application explains that crude *cannabis* extracts are known to contain high concentration of waxes and other hydrocarbons from plant materials. Such waxes and plant materials are typically removed or reduced by a "winterization process" prior to decarboxylation and purification of the *cannabis* extract. The "winterization process" is typically performed by dissolving the distillate in alcohol which is then subjected to subzero temperatures to separate out the fats and waxes. In the '500 application, the winterization process involves dissolving the distillate in 200-proof ethanol and then placing in the solution in a freezer at −20° C. for 4 hours. While cold, the precipitated material containing the unwanted fats and waxes is filtered out using a filter funnel and the filter was rinsed with 100 ml of ice cold ethanol. The filtered ethanolic solution of the distillate was evaporated to dryness to give 84.0 g residue (78% CBD content). The '500 application described that the CBD recovery in this step is 99.0%, demonstrating that the typical extraction process focuses on removing waxes and lipids during the extraction process, in favor of producing a concentrated cannabinoid residue or extract.

Surprisingly, it has been found that a fraction that is typically discarded, containing the waxes and lipids, is important to the therapeutic value of the extract. This is because it is becoming recognized that the plant's therapeutic value may not be attributable to the major cannabinoids alone. Rather, the therapeutic value may lie in a synergistic effect between numerous chemical components present in the *cannabis* plants. The plant is believed to contain over a hundred cannabinoids, numerous secondary metabolites of *cannabis*, terpenes and terpenoids, all of which are hypothesized to contribute synergistically to the plant's therapeutic benefits. This interaction or synergy resulting from the complex mixture of compounds present within the *cannabis* plant is variously known as the "entourage effect," in which a mixture of compounds present demonstrates greater therapeutic efficacy than any of its constituent compounds in isolation.

Capturing the non-cannabinoid portions of the extract that would assist in preserving the "entourage effect," while removing plant matter that may detract from the stability or safety of the formulation during the extraction process is challenging. When breaking down the plant matter, the initial extract contains particulate materials, chlorophyll, large sugars, such as plant cellulose, and proteins that may not have the desired effects and impact other aspects of the product, such as its shelf-life and stability. Thus, there is a need to develop an extraction process whereby undesirable plant materials are removed, but desirable waxes and lipids, which assist in creating the "entourage effect", are not inadvertently discarded. This portion of the extract, called the "remainder", which contains the desirable waxes and lipids, may also be removed prior to the cannabinoids being decarboxylated. High temperatures typically used during decarboxylation processes may destroy the desirable waxes and lipids in the remainder or convert them into "sand-like" particles which are undesirable in an extract.

The decarboxylation of compounds, such as THCA and THCVA, to form psychoactive or physiologically active compounds, such as Δ9-THC and THCV is typically accomplished by heating the extract (or by directly heating the plant material). A major drawback of oven-based decarboxylation is the tendency to cause the loss of desirable volatile compounds, such as caryophyllene and other terpenes, through evaporation or heat-induced chemical reactions. Accordingly, a process is needed to enable a greater degree of control over the decarboxylation of *cannabis* extracts.

SUMMARY OF THE INVENTION

The present invention is a process for producing various types of *cannabis* extract from harvested *cannabis*. A quantity of harvested *cannabis*, which typically includes the inflorescence, floral leaves, and small stems of a flowering *cannabis* plants, is pre-frozen. The harvested *cannabis* is first subjected to cryogenic grinding to produce pulverized *cannabis*. The pulverized *cannabis* is then subjected to alcohol extraction to produce an initial *cannabis* extract, which can be subjected to one of several forms of further processing according to the desired chemical profile of the final product. The initial *cannabis* extract may be further fractionated to remove a particulate "remainder fraction" and the resulting cannabinoid fraction may then be subjected to chemical processing that promote the conversion of THCA to Δ9 THC; the conversion of THCVA to THCV; the conversion of THCA to cannabinol ("CBN"); or the conversion of THCA to Δ8-tetrahydrocannabinol (Δ8-THC). The various fractions can be mixed in various proportions. The presence or absence of the remainder fraction does not significantly affect subsequent fractionation; however if the remainder fraction is captured, it can be used to augment the other fractions.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a *cannabis* extraction method that produces a biologically active remainder fraction.

The present invention is a process that includes several stages, which are described below as Stages 1-2, 3A-3C, and 4. Where the process refers to the use of "alcohol," a solution containing at least 99% ethanol by volume or at least 99% isopropyl alcohol by volume is preferred although concentrations as low as about 95% alcohol can be used. Specifically, "ethyl alcohol 200 proof" or "99.9% isopropyl alcohol" supplied by Green Wood Cleaning Products, Inc., of Hollister, Calif., may be used.

Stage 1: Cryogenic Grinding

Figure 1:
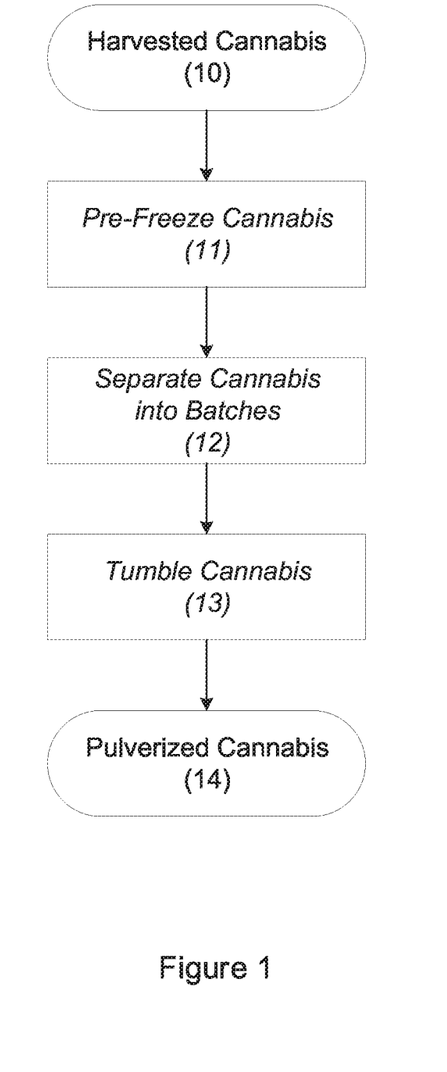
FIG. 1 is a flow diagram showing the steps for converting harvested *cannabis* to pulverized *cannabis* through cryogenic grinding.

Referring to FIG. 1, cryogenic grinding is used to convert a quantity of harvested *cannabis* 10 into pulverized *cannabis* 14. The harvested *cannabis* 10, which may be fresh or cured, should be pre-frozen (step 11) at a temperature of about −29° C. (−20.2° F.) prior to processing. Cryogenic grinding should take place at an ambient temperature of 0-10° C. (32-50° F.). An ambient temperature of 0° C. (32° F.) is preferable for minimizing the loss of compounds from the harvested *cannabis* through evaporation or chemical reactions that would occur at higher temperatures, but acceptable results can be obtained when the ambient temperature is as high as 10° C. (50° F.). In practice, it is advisable to perform cryogenic grinding in a cold room or a walk-in freezer.

When pre-freezing is complete, the harvested *cannabis* is separated into batches (step 12) weighing approximately 450 g (approx. 1.0 lb) each. For each batch, the harvested *cannabis* is placed into a plastic bag capable of accommodating a volume of approximately 15 cm×48 cm×20 cm (6 in.×19 in.×8 in.). A Reynolds® turkey-size oven cooking bag may be used. The bag is then sealed; sealing may be accomplished by tying the open end of the bag into a knot or with a suitable fastener, such as twist tie. The batches of harvested *cannabis* are then processed in a tumbling apparatus (step 13).

The tumbling apparatus is a horizontally oriented cylindrical drum that is capable of rotating about its own axis. The drum should be capable of performing approximately 40 rotations per minute (rpm). The drum may have a diameter of approximately 60 cm (24 in.) and a length of approximately 91 cm (36 in.). A Triminator® Dry *cannabis*-trimming machine supplied by Dana Mosman of Boulder, Colo., may serve as the tumbling apparatus.

Five bags of harvested *cannabis* are placed into the tumbling apparatus. Approximately 680 g (approx. 1.5 lb) of dry ice (i.e., solid carbon dioxide) is placed into the tumbling apparatus along with the bags of harvested *cannabis*. The dry ice may be in the form of uniformly sized cylindrical pieces that are approximately 0.64 cm (0.25 in.) in diameter and approximately 5.0 cm (2.0 in) in height. Dry-ice "nuggets" supplied by Praxair Technology, Inc., of Danbury, Conn., may be used.

The bags of harvested *cannabis* are tumbled at approximately 40 rpm for about 10 minutes. The appropriate rotational speed can be achieved with a Triminator® Dry *cannabis*-trimming machine or with a rheostat controlling the motor speed of a dedicated tumbler. During the tumbling process, the agitation of the harvested *cannabis* within each bag, in conjunction with the physical impacts of the dry ice against the bag, pulverize the harvested *cannabis* to a fine powder, thereby producing pulverized *cannabis* 14.

It will be appreciated that the amount of *cannabis* that can be processed by the tumbling apparatus depends on the size of the tumbling apparatus. The equipment can readily be scaled up for larger amounts of *cannabis*.

Stage 2: Alcohol Extraction

Figure 2:
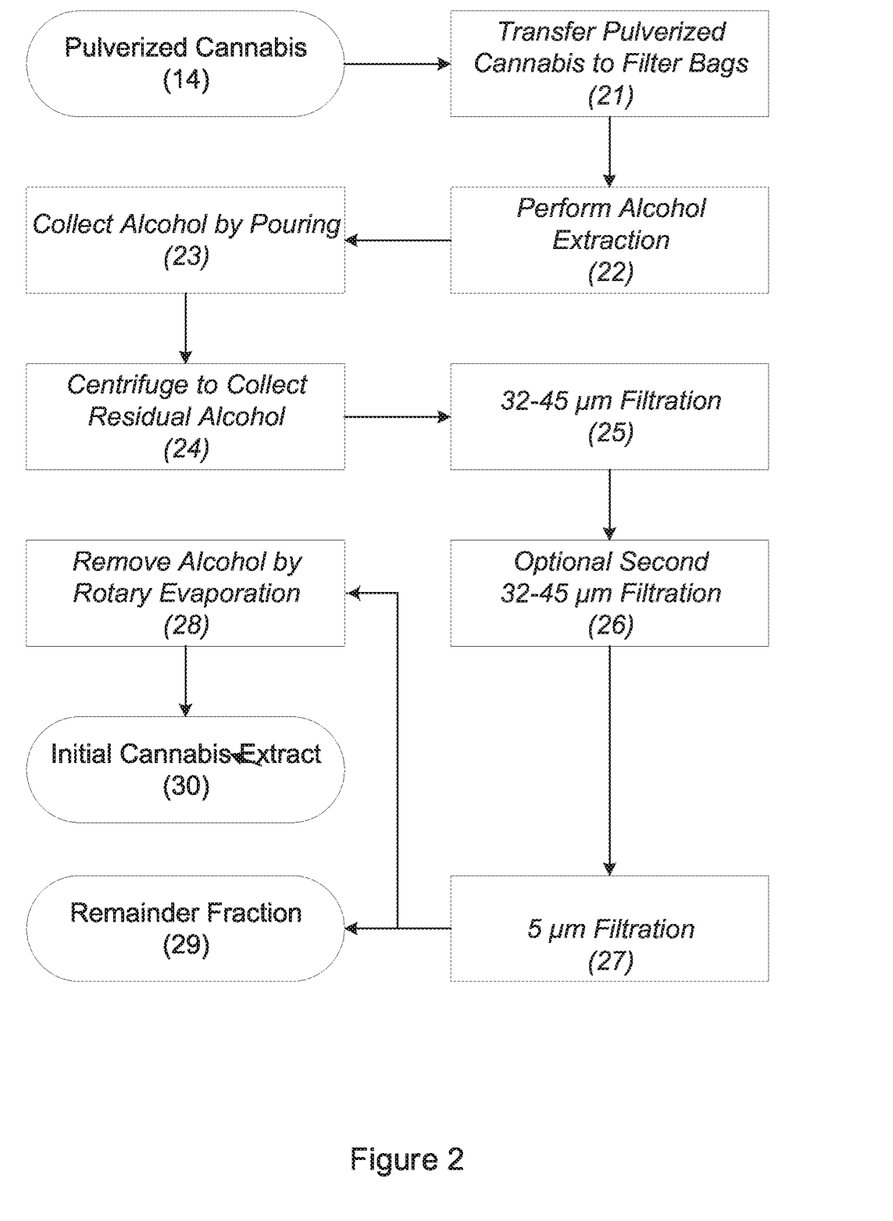
FIG. 2 is a flow diagram showing the steps for converting pulverized *cannabis* to an initial *cannabis* extract using alcohol extraction.

Referring to FIG. 2, alcohol extraction is used to separate the compounds present within the pulverized *cannabis* from solid plant matter. In preparation for alcohol extraction, the bags of pulverized *cannabis* 14 are removed from the tumbling apparatus and transferred into filter bags (step 21). Each batch of *cannabis* is transferred from the plastic bag used during cryogenic grinding to a filter bag having a pore diameter of about 220 µm. The filter bag should be sufficiently large to accommodate the pulverized *cannabis* without deliberate packing. A Bubble Bags® filter bag with a nominal capacity of 3.78 L (1 gal) and a pore diameter of 220 µm supplied by Fresh Headies Internet Sales Ltd. of Vancouver, Canada, may be used. Transfer of the pulverized *cannabis* is preferably performed at the same ambient temperature as cryogenic grinding to prevent premature warming of the pulverized *cannabis*.

Two filter-bags of pulverized *cannabis* are placed into an extraction apparatus for alcohol extraction (step 22). The extraction apparatus is an upright cylindrical drum that is capable of rotating about its own axis. The drum can have a diameter of approximately 38 cm (15 in.) and height of approximately 38 cm (15 in.) and should be capable rotating at 40 rpm. The extraction apparatus is prefilled with approximately 40 L (10 gal) of alcohol. The alcohol should completely immerse the filter bags without a risk of overflowing from the extraction apparatus. The alcohol is preferably pre-chilled to −30° C. (−22° F.) to minimize undesirable extraction of chlorophyll and lipid material from the pulverized *cannabis*. The extraction process, however, will produce acceptable results with an alcohol temperature as high as 0° C. (32° F.). To maintain chilling of the alcohol during the extraction process, the extraction apparatus may be placed in a chest freezer or cold room.

Once immersed, the drum of the extraction apparatus is rotated at approximately 40 rpm for 10 minutes, during which compounds from the pulverized *cannabis* dissolve into the alcohol. The alcohol normally takes on a bright-green color as extraction proceeds. The alcohol is then poured from the extraction apparatus for collection (step 23). The filter bags, which remain in the extraction apparatus, are subjected to centrifugation at 200 g to spin out any residual alcohol that remains within the filter bags (step 24). The filter bags may be manually rearranged within the extraction apparatus prior to centrifugation to ensure adequate balance. The residual alcohol is combined with the alcohol obtained by pouring.

The alcohol extract is then passed through a stainless-steel mesh filter or other filter type with a pore diameter of about 32 µm-45 µm (step 25), and the filtrate (the "first-pass or first filtrate") is collected. The first-pass filtrate can optionally be passed through the same filter again (step 26), and the resulting twice-filtered liquid (the "second-pass filtrate") is collected. An 8-inch diameter test sieve with a pore opening size of 32 µm (No. 450) supplied by W.S. Tyler (a division of Haver Tyler, Inc.) of Mentor, Ohio, may be used as the filter. The filtration step(s) is(are) intended to remove undissolved particles of plant material from the solvent. Prior to filtration through the about 32 µm-45 µm filter, the solution is somewhat cloudy. After filtration, the solution is clearer. Additional optional filtration through a 5 µm filter was found to produce an essentially clear final filtrate (step 27). Either the initial (32 µm-45 µm) filtrate or the 5 µm filtrate can be further processed for decarboxylation as detailed below. That is to say, the optional 5 µm filtration step does not significantly affect the subsequent decarboxylation steps.

As detailed in U.S. Pat. No. 10,471,113 (the contents of which are incorporated herein by reference), the material, which is known as the "remainder" fraction, removed by the 5 µm filter can be recovered from the surface of the filter (step 29) and used in therapeutic formulations. The remainder fraction from extracts performed at −30° C. (−22° F.) is a largely colorless cake whose precise composition has not yet been determined. When extraction takes place at a higher temperature (about 0° C. [32° F.]), the volume of remainder is larger and has a distinct green chlorophyll color. It is believed that the remainder is primarily micelles of plant waxes, other lipid materials as well as carbohydrates. It may also contain very small particles of undissolved plant material. It has been unexpectedly found that adding significant quantities of the remainder fraction to various medicinal or even recreational formulations intended for oral administration significantly augments the activity of these formulations. It is believed that some compounds within the remainder fraction interact with active *cannabis* compounds in the formulations to produce an enhanced "entourage" effect. Alternately or additionally, lipids or other compounds in the remainder fraction could enhance absorption of the formulation thereby increasing observed activity. Because of the great utility of the remainder fraction, use of the 5 µm filtration step and recovery of the remainder fraction has become the preferred procedure. The remainder fraction, if used immediately upon collection, may be added directly to *cannabis* formulations. If intended for later use, the remainder fraction may be suspended in ethanol, and stored at low temperatures for extended periods. Prior to use, the resuspended remainder may be recovered through pelleting by centrifugation or through filtration. Filtration appears to be the easiest way of separating the remainder from the primary extract, but it will be appreciated that similar results can be achieved with alternate separation technologies such as centrifugation.

Regardless of which separation technology is employed and how many filtration steps are used, the final filtrate (step 28) is subjected to rotary evaporation at about 40° C. (104° F.) at a reduced pressure of about 5332 Pa (40 Torr or 0.05 atm) until substantially all of the alcohol is removed. The liquid that remains is the Initial *Cannabis* Extract 30, which may be stored or subjected to one of the further processing steps designated as Stages 3A-3C below. For every two filter-bags of pulverized *cannabis*, the extraction process produces approximately 300 ml of initial *cannabis* extract. The initial *cannabis* extract is preferably stored at 0° C. (32° F.) while awaiting further processing.

A CUP-30 Centrifuge Utility Platform Alcohol Extraction System (the "CUP-30 system") made by Delta Separations LLC of Santa Rosa, Calif., may serve as the extraction apparatus. The ratio of alcohol to pulverized *cannabis* described above (i.e., approximately 40 L of alcohol for every 2 filter-bags of pulverized *cannabis*) may be scaled up to fully use the processing capacity of the CUP-30 system.

Stage 3A: Conversion of Tetrahydrocannabinolic Acid in the Initial *Cannabis* Extract to Delta-9-Tetrahydrocannabinol Referring to FIG. 3, a first diluted solution 31 is produced by diluting the initial *cannabis* extract 30 to 120% of its initial volume using alcohol. For example, 80 ml of initial *cannabis* extract 30 should be combined with enough alcohol to produce 100 ml of the first diluted solution. The volume of the first diluted solution is further increased by 3%-5% through the addition of water to produce a second diluted solution (step 32). For example, 100 ml of the first diluted solution may be combined with enough water to make 103-105 ml of the second diluted solution. The presence of the water within the second diluted solution inhibits the undesirable formation of cannabinol ("CBN") as well as the degradation of terpenes and cannabinoids. This dilution step also prevents the thermal decomposition of the remainder fraction if it has not previously been removed through filtration. After thermal decomposition, the remainder adds gritty particulates to the product.

Figure 3:
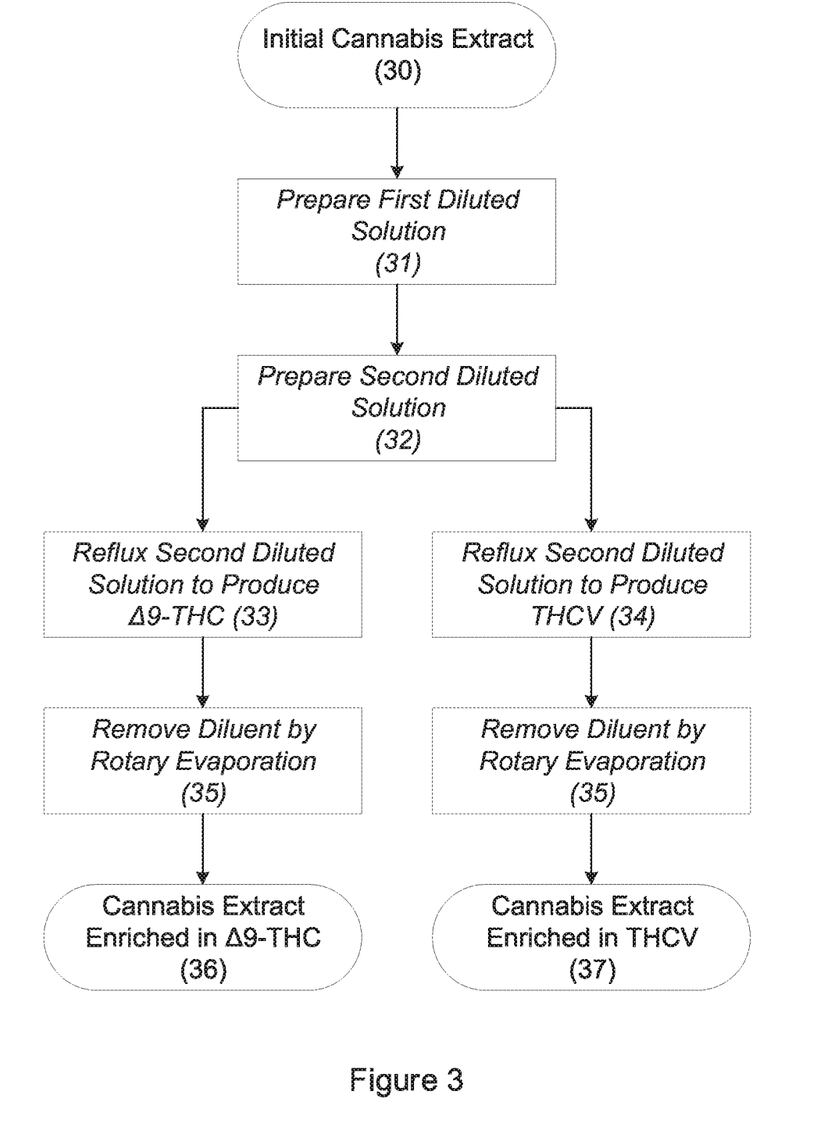
FIG. 3 is a flow diagram showing the steps for producing Δ9-THC and THCV via decarboxylation of an initial *cannabis* extract.

The second diluted solution is refluxed at 80-100° C. for 1-3 hours, preferably 80° C. for 2 hours, to promote the decarboxylation of THCA to form Δ9-THC (step 33). Acceptable results can be obtained by refluxing at 100° C. for 1 hour, although the higher temperature may result in an increase in the undesirable formation of CBN. Refluxing is performed in a flask with an attached cold "finger" or condenser whose temperature is −30° C. to −40° C., preferably −40° C. The cold condenser may be cooled by propylene glycol circulated by an external chiller. Following refluxing, the second diluted solution is subjected to rotary evaporation (step 35) until substantially all of the diluent is removed. The liquid that remains is a refined *cannabis* extract enriched in Δ9-THC 36.

Refluxing may be used to process the initial *cannabis* extract in batches of 300 ml. Batch sizes may be adjusted according to the capacity of the refluxing apparatus.

Stage 3B: Conversion of Tetrahydrocannabivaric Acid in the Initial *Cannabis* Extract to Tetrahydrocannabivarin Referring to FIG. 3, the initial *cannabis* extract 28 is converted to a first diluted solution and then a second diluted solution (steps 31 and 32) as in Stage 3A above. The second diluted solution is refluxed for 1-2 hours, preferably 1.5 hours, at a temperature of 120° C. to promote the decarboxylation of THCVA to form THCV (step 34). Refluxing is performed in a flask attached to a cold condenser whose temperature is −30° C. to −40° C. The cold condenser may be chilled as in Stage 3A above. Following refluxing, the second diluted solution is subjected to rotary evaporation (step 35) until substantially all diluent is removed. The liquid that remains is a refined *cannabis* extract that is enriched in THCV 37.

Stage 3C: Increasing Cannabinol Content of Initial *Cannabis* Extract

Figure 4:
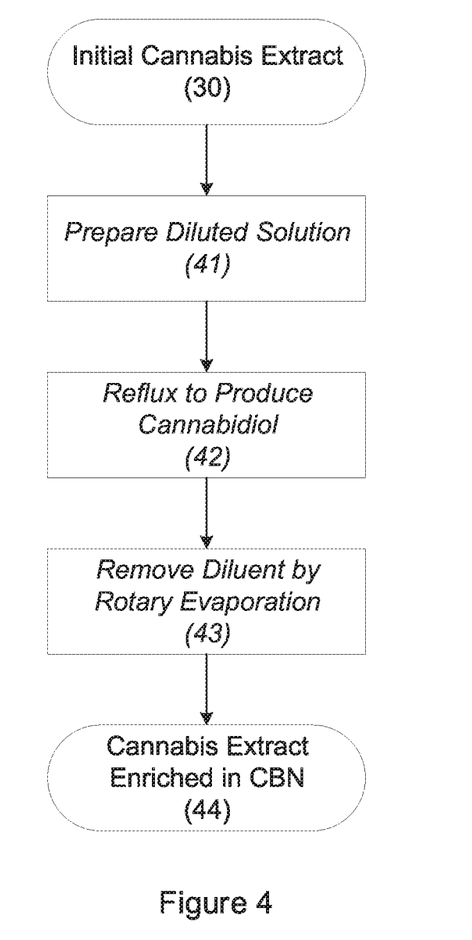
FIG. 4 is a flow diagram showing the steps for producing cannabinol via decarboxylation of an initial *cannabis* extract.

Referring to FIG. 4, the initial *cannabis* extract 28 is diluted with alcohol to a concentration of 80% by volume to produce a diluted solution 41. For example, 80 ml of initial *cannabis* extract 30 should be combined with enough alcohol to produce 100 ml of the diluted solution. The diluted solution is refluxed at 180° C. for 1-3 hours, preferably 2 hours, to promote the formation of cannabinol (step 42). Following refluxing, the diluted solution is subjected to rotary evaporation (step 43) until substantially all alcohol is removed. The liquid that remains is a refined *cannabis* extract that is enriched in cannabinol 44.

Referring to FIG. 4, the initial *cannabis* extract 30 is converted to a refined *cannabis* extract enriched in Δ9-THC 36 according to the steps in Stage 3A above.

Stage 4: Increasing Δ8-Tetrahydrocannabinol Content of the Initial *Cannabis* Extract Referring to FIG. 5, the volume of the refined *cannabis* extract 36 is then increased by 7.5%-15%, preferably 10%, by the addition of powdered bleaching clay (step 51). T-41 Canna Bleach supplied by Carbon Chemistry Ltd. of Watkins, Colo., may be used. The volume of refined *cannabis* extract is then increased by another 7.5%-15%, preferably 10%, by the addition of activated charcoal in powdered form (step 52). The volume of powdered bleaching clay added should be essentially identical to the volume of activated charcoal added. Carbon Powder A supplied by Summit Research of Scotts Valley, Calif., may be used. For example, 100 ml of refined *cannabis* extract may be combined with 7.5 cm$^3$ of specialty bleaching clay and 7.5 cm$^3$ of activated charcoal to produce a mixture having a final volume of 115 ml.

Figure 5:
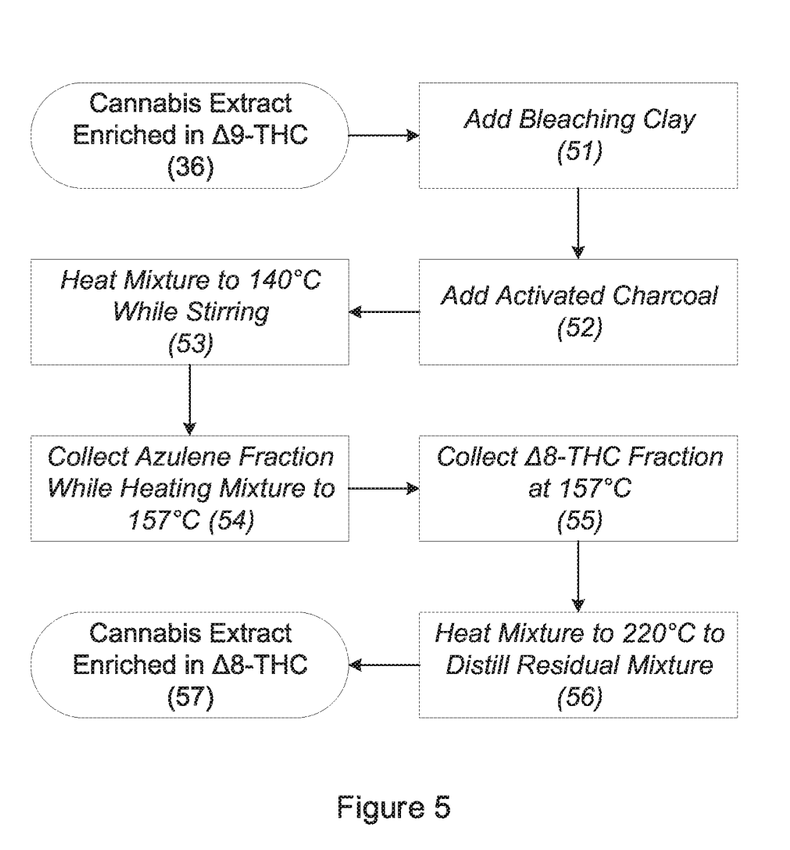
FIG. 5 is a flow diagram showing the steps for producing Δ8-THC via decarboxylation of a *cannabis* extract containing Δ9-THC.

The resulting mixture is subjected to distillation using a short-path distillation apparatus (the "distillation apparatus"). The distillation apparatus is composed of a feed flask, which contains the mixture. The feed flask is placed on a combination hotplate-magnetic stirrer, which allows a liquid within the feed flask to be simultaneously heated and agitated by a stir bar. The feed flask is attached to a condenser, which, in turn, is preferably attached to a "triple cow"-style distillation receiver with a connection point for a vacuum source. Two flasks are connected to the distillation receiver, the first for collecting undesirable distillates (the "waste flask"); and the second for collecting desirable distillates (the "collection flask"). Unneeded connections on the distillation apparatus should be sealed with stoppers. The temperature of the condenser is maintained at 21-23° C. (70-74° F.) by the circulation of water. A distillation receiver (Mfr. No. CG-1276-01) supplied by Thomas Scientific LLC of Swedesboro, N.J., may be used.

The mixture is placed into the feed flask, and the waste flask is placed in a position to receive distillate. The distillation apparatus is connected to a vacuum source, and the pressure within the distillation apparatus is reduced to approximately 66.7 Pa (500 mTorr or $6.7 \times 10^{-4}$ atm). The mixture is gradually heated to 140° C. while being agitated by the stir bar (step 53). It is important to ensure that the mixture does not foam (or "muffin") during distillation. Uncontrolled foam may expand to reach and contaminate the condenser, making the distillate unsuitable for use. To minimize foaming, it is advisable to set the stir bar to an initial speed of 400 rpm. The mixture is then gradually heated at a rate of approximately 15° C. per minute, and speed of the stir bar increased at a rate of approximately 50 rpm per minute, until the mixture reaches 140° C. and the stir bar reaches 900 rpm. Any distillate that incidentally emerges during the initial heating process is collected in the waste flask.

Once the mixture reaches about 140° C., the distillate should take on a bluish color as azulene and derivatives thereof begin to distil from the mixture. Heating of the mixture should continue at the rate of approximately 1° C. per minute until the mixture reaches 157° C. During the heating period, bluish distillate continues to distill from the mixture and is collected in the waste flask (step 54). The temperature of the mixture is maintained at 157° C. until the condensing distillate is colorless, at which point all azulene and derivatives thereof have been removed from the mixture.

The colorless distillate is collected in the collection flask, which should be rotated into position as soon as bluish distillate stops appearing. The temperature of the mixture is further increased at the rate of approximately 1° C. per minute until it reaches 175'C. The distillate, which now contains Δ8-THC, continues to be collected in the collection flask during this period (step 55). The mixture is maintained at a temperature of 175° C. until substantially all of the liquid in the feed flask is depleted. The mixture is then heated to 220° C., and distillate is collected until no further distillate is produced (step 56). The final heating to 220° C.

promotes the full conversion of liquid remaining in the feed flask to the vapor phase. The distillate is a refined *cannabis* extract enriched in Δ8-THC 57.

The refined *cannabis* extract enriched in Δ8-THC 57 should be colorless. If the distillate in the collection flask has a noticeable color, such as amber or teal, the distillate should be treated as the *cannabis* extract enriched in Δ9-THC 36 and subjected to a second round of processing according to steps 51-56.

The following claims are thus to be understood to include what is specifically illustrated and described above, what is conceptually equivalent, what can be obviously substituted and what incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method of producing a refined, decarboxylated *cannabis* extract comprising: a) freezing a quantity of *cannabis* to make frozen *cannabis*; b) grinding the frozen *cannabis* at cryogenic temperatures to produce pulverized *cannabis*; c) extracting the pulverized *cannabis* with a quantity of alcohol; d) separating the alcohol from the pulverized *cannabis* to obtain an initial *cannabis* extract; e) diluting the initial *cannabis* extract with a quantity of alcohol to produce a first diluted initial *cannabis* extract; f) adding a quantity of water to the first diluted initial *cannabis* extract to produce a second diluted initial *cannabis* extract; and g) refluxing the second diluted initial *cannabis* extract at a temperature of about 80.degree. C.-120.degree. C. for a period of about 1-3 hours whereby the second diluted initial *cannabis* extract is decarboxylated to produce the refined, decarboxylated *cannabis* extract.

2. The method of claim 1, further comprising adding a quantity of bleaching clay and a quantity of activated charcoal to the refined, decarboxylated *cannabis* extract to produce a mixture and distilling the mixture at a temperature of about 157.degree. C.-220.degree. C. to produce a refined *cannabis* extract enriched in Delta 8-tetrahydrocannabinol.

\* \* \* \* \*